(12) United States Patent
Pommereau et al.

(10) Patent No.: US 7,214,212 B2
(45) Date of Patent: May 8, 2007

(54) CAP FOR INJECTION DEVICES

(75) Inventors: Christian Pommereau, Otterberg (DE); Carsten Larsen, Kronberg (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/866,904

(22) Filed: Jun. 14, 2004

(65) Prior Publication Data

US 2005/0020989 A1    Jan. 27, 2005

Related U.S. Application Data

(60) Provisional application No. 60/516,903, filed on Nov. 3, 2003.

(30) Foreign Application Priority Data

Jun. 13, 2003   (DE)   ................. 103 27 119

(51) Int. Cl.
*A61M 5/32* (2006.01)
(52) U.S. Cl. ..................................... 604/192
(58) Field of Classification Search ............... 604/192, 604/198, 263; 401/257, 104, 131, 243, 244, 401/247
See application file for complete search history.

(56) References Cited

U.S. PATENT DOCUMENTS

| | | | |
|---|---|---|---|
| 2,800,816 A | | 7/1957 | Tasciotti |
| 3,830,574 A | * | 8/1974 | Glombitza et al. .......... 401/195 |
| 3,889,673 A | * | 6/1975 | Dovey et al. ................ 604/192 |
| 4,493,575 A | * | 1/1985 | Mutschler ................... 401/195 |
| 4,952,088 A | * | 8/1990 | Groetsch .................... 401/195 |
| 5,114,406 A | | 5/1992 | Gabriel et al. |
| 5,125,912 A | | 6/1992 | Kinnel |
| 5,305,766 A | | 4/1994 | Hahn |
| 2003/0093037 A1 | | 5/2003 | Parker et al. |

FOREIGN PATENT DOCUMENTS

| | | |
|---|---|---|
| EP | 0 327 910 A2 | 8/1989 |
| EP | 0 450 905 A1 | 10/1991 |
| EP | 0 496 141 A1 | 7/1992 |
| EP | 0 498 737 A1 | 8/1992 |
| EP | 0 594 349 A1 | 10/1992 |
| EP | 1 074 273 A1 | 2/2001 |
| WO | WO 87/02895 | 5/1987 |
| WO | WO 88/06463 | 9/1988 |
| WO | WO 90/03198 | 4/1990 |
| WO | WO 93/16740 | 9/1993 |
| WO | WO 96/36233 | 11/1996 |
| WO | WO 97/36625 | 10/1997 |
| WO | WO 99/38554 | 8/1999 |
| WO | WO 02/05147 A1 | 1/2002 |
| WO | WO 02/076535 A1 | 10/2002 |
| WO | WO 03/011371 A2 | 2/2003 |

* cited by examiner

*Primary Examiner*—Sharon E. Kennedy
(74) *Attorney, Agent, or Firm*—Paul R. Darkes

(57) ABSTRACT

The present invention concerns a cap suitable for injection devices having an exchangeable needle assembly, which serves as a mounting/demounting tool of the said needle assembly.

4 Claims, 3 Drawing Sheets

Figure 2A:
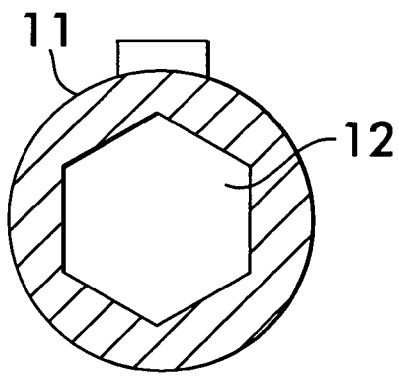

FIG.IA
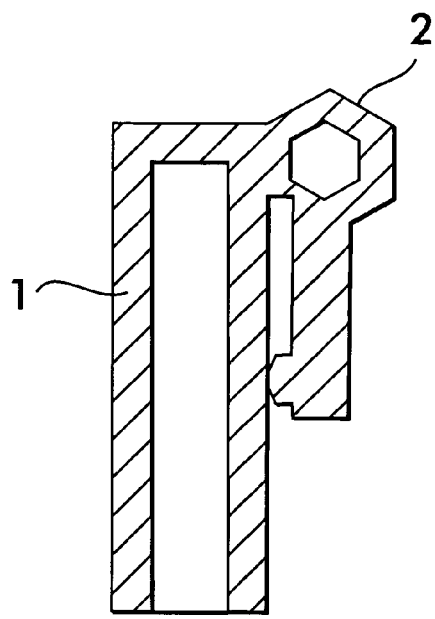
FIG.IB
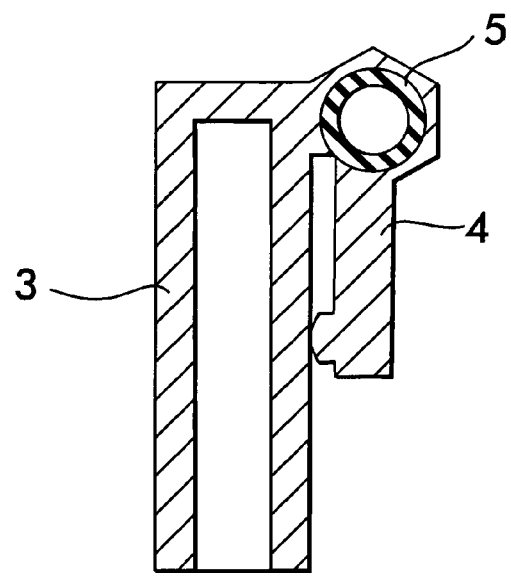
FIG.IC
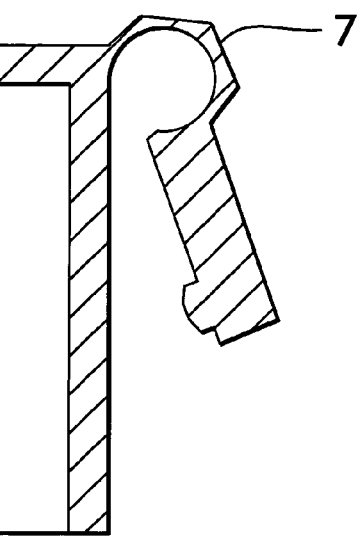
FIG.ID
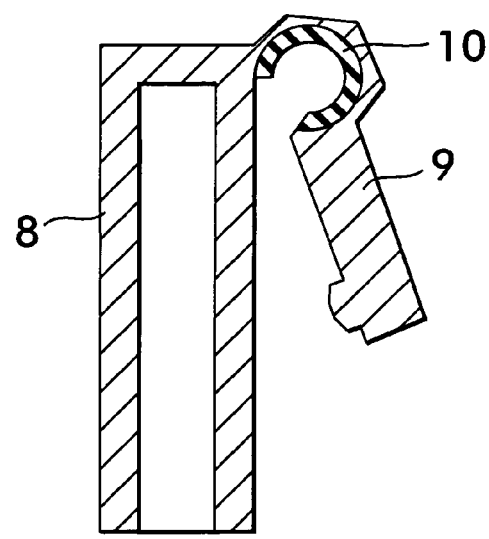

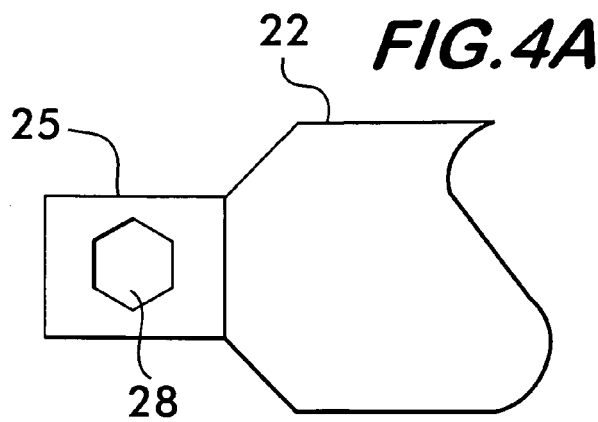
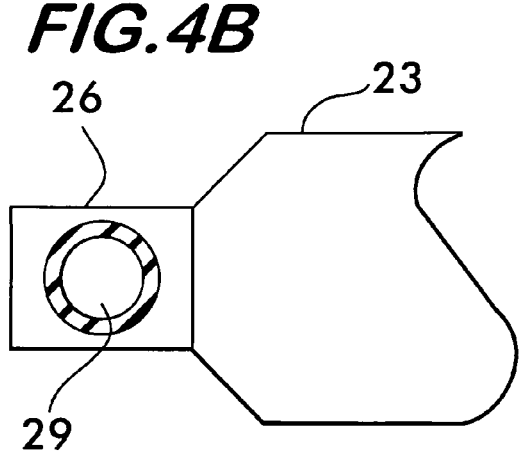
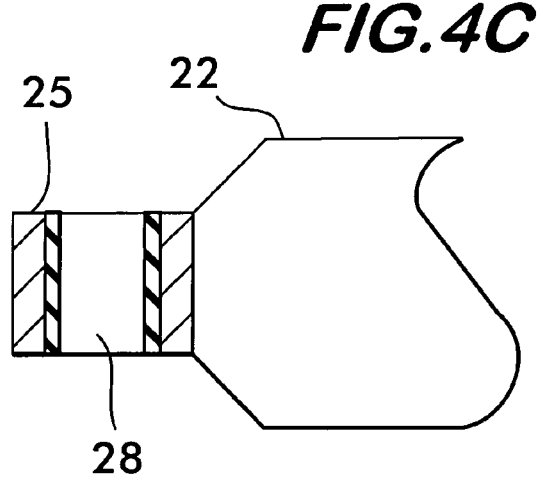
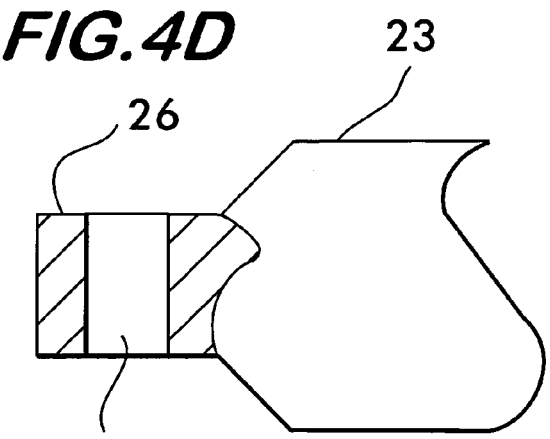
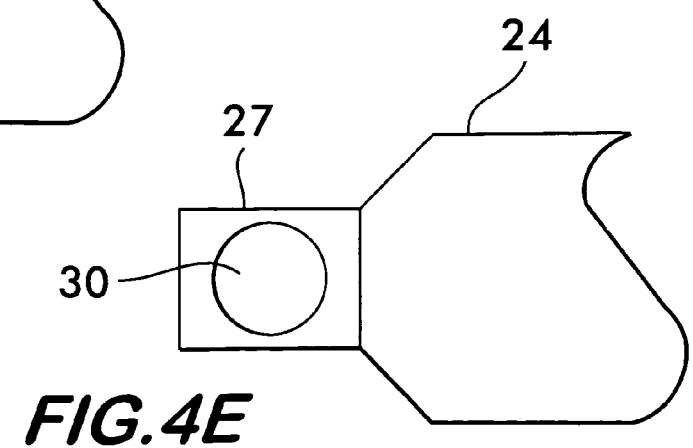

CAP FOR INJECTION DEVICES

This Application claims priority from German Application No. 10327119.8 filed on Jun. 13, 2003, and from U.S. Provisional Application No. 60/516,903 filed on Nov. 3, 2003, which is hereby incorporated by reference herein in its entirety.

The present invention concerns a cap suitable for injection devices having an exchangeable needle assembly, which serves as a mounting/demounting tool of the said needle assembly.

Injection devices having exchangeable needle assemblies are well known from numerous patent publications, such as EP-A1-245312, EP-A1-268191, EP-A2-327910, EP-A1-594349, EP-A1-496141, EP-A1-450905, EP-A1-498737, WO 97/36625 A1, EP-A1-1003581, and WO2003011371 A1.

Some of these injection devices are named "pen-type devices" or "pens" due to their essentially longitudinal shape, and the fact, that the device comprises a cartridge containing the drug to be delivered. There are disposable and reusable pens. Generally, both pen types comprise a cartridge containing the drug or pharmaceutical composition to be delivered. It is a particular feature of the reusable pen, that the medicament cartridge may be removed when it is empty and the device may be reloaded with a new one. In contrast, the exchange of the cartridge is not intended in case of the disposable pen, which shall be discarded, when the medicament reservoir (mostly a cartridge) is empty.

This type of injection devices is suitable for the subcutaneous/transdermal application of pharmaceutical compositions, e.g., in the area of diabetes (e.g., insulins, insulin derivatives), treatment or prophylaxis of thrombotic diseases (e.g., heparins, heparin derivatives), treatment by use of growth hormones or vaccination. The injection devices are designed for self-administration of the drug by the patient, as this is required, e.g., for diabetic people, or for the treatment of other diseases, where a long-term treatment is required with regular dosages of a subcutaneous applicable medicament. However, similar or identical injection devices may also be suitable in animal health or vaccination.

Generally, this type injection devices at least comprise a housing consisting of one or more parts, a medicament reservoir of a (liquid or suspended) drug to be delivered, a dosage and drug delivery mechanism (e.g., piston, drive mechanism, dosage mechanism, dispensing mechanism), which allows precise dosage and application of a pre-selected amount of medicament, an injection needle system, and a cap.

The medicament reservoirs of the said devices are mostly designed according to the principle function of a cartridge, whereby the drug is expelled by a movable piston and applied to the patient through an injection needle.

In some cases, the injection needle system (needle assembly) may further contain a particular "needle cap" (which is different from the cap of device).

The skilled person in the art is well aware about many options and technologies how to design or realize the specific design or construction of each of the required elements (optionally, mechanical, electrical, or electronically equipped or supported elements) of such an injection device (such as a housing, medicament reservoir (cartridge), drive mechanism, dosage mechanism, dispensing mechanism, needle assembly, cap etc.).

Generally, the medicament dose, which shall be applied to the patient, is set by a suitable dosage setting and release mechanism and expelled by use of an injection needle (e.g., needles of 29 to 33 Gauge). Injection needles suitable for subcutaneous or hypodermal application of pharmaceutical compositions are of 3–18 mm, mostly 5–13 mm length.

After set up of the needle assembly on the device, the injection needle shall regularly be exchanged preferably after each injection in order to safeguard sterility of the system and avoidance of infections. Accordingly, a regular exchange of the needle is crucial for the patient.

As a matter of fact, many patients (e.g., elderly or diabetic people) may not be able to exchange the needle or needle assembly as it would be required for the abovementioned reasons.

The reason therefore may be any disability with respect to the eyes, fingers, and the like. This may then lead to an increased risk of injury by needle stick for such people or, alternatively, may increase the risk of infection, if the needle/needle assembly is not regularly exchanged.

Here, the present invention will reduce these risks and enable the said patient group to safely exchange the needle assembly without any assistance. In addition, other users of the invention, such as doctors or nurses, may also take advantage of the present invention.

The above-mentioned problem is solved by the technical elements of the present invention. Accordingly, a first aspect of the present invention is a cap for an injection device, wherein said injection device comprises an exchangeable needle assembly, and wherein said cap can be fixed on the device in order to cover the said exchangeable needle assembly, and wherein the said cap comprises a receiving bore, characterized in that, the said cap having the receiving bore is designed to receive the said needle assembly.

Consequently, the present invention provides a mounting/demounting means/tool, which is particularly easy to use for the above-mentioned patient groups and is adapted to the particular geometry of the needle assembly of such injection devices.

According to the present invention the subsequently mentioned terms shall have—beside the general understanding of the person skilled ion the art—the following preferred meaning:

An "injection device" means any injection device comprising a cap, e.g., pen-type injection devices known from EP-A1-828527, EP-A1-581924, EP-A1-498737, WO2003/011371, EP-A1-1074273 or other types of injection devices comprising a cap, e.g., known from WO2002/051471A1 or WO2002/076535A1.

An "exchangeable needle assembly" means any needle assembly, respectively, needle holder of an injection device comprising an injection needle, which is designed to be removed by the user (as it would be required to ensure that a clean needle is used by the user or patient). Usually, the said needle assembly has to be screwed or otherwise fixed onto the housing containing the cartridge.

Therefore, the needle assembly may be designed so that it is easy to mount/demount (or lock/unlock), e.g., by having a structured surface, or the design of a hexagonal or multi-edge bolt/screw.

Preferably, the needle and/or injection device is designed for transdermal or subcutaneous application of pharmaceutical compositions for the application to humans or animals.

Particularly preferably, the needle and/or injection device is designed for the application of insulin, insulin derivatives or analogous, heparin, heparin derivatives or analogous, growth hormones and the like.

A "cap" according to instant invention may be any suitable cover of at least the needle assembly of an injection device, optionally comprising a clip and/or attachment (see e.g., FIGS. 1 to 4). Furthermore, a "cap" according to instant invention may be the original cap of an injection device or an attachment or fitting which can be attached to the original cap of the injection device and is form- and/or force-locking with the original cap.

A "cap, which can be fixed on the device shaft" means any cap, which may be screwed (in and out), clipped, or otherwise fixed on the shaft of an injection device.

A "receiving bore" of the cap means any receiving bore, which fits to the needle assembly in order to allow mounting/ demounting of the exchangeable needle assembly on the injection device. The receiving bore is formed/designed by the cap, by the optional clip, by any attachment of the cap, or by any combination of said cap, clip and attachment. The receiving bore may be designed like a spanner (allen, box, ring, hexagonal, multi-edge) or wrench, which are optionally adjustable to the size of the diameter of the needle assembly. Alternatively, the inner surface of the receiving bore may be covered by or is consisting of any material, which may have a suitable friction coefficient, e.g., by increased roughness of the surface and/or elastic properties of the used material (such as gum, suitable plastics, or treated surfaces) and are suitable to mount/demount the said needle assembly of the injection device.

A second aspect of the present invention is an injection device comprising a cap of the invention.

A third aspect of the present invention is an exchangeable needle assembly having the geometry of a hexagonal, or multi-edged screw or bolt, and which fits to the receiving bore of the cap of the invention.

A fourth aspect of the present invention is the use of a cap of the invention for mounting/demounting a needle assembly on an injection device.

A fifth aspect of the present invention is the use of a needle assembly of the invention in an injection device comprising a cap of the invention.

A sixth aspect of the present invention is a kit comprising a cap of the invention, an exchangeable needle assembly of the invention, and/or an injection device of the invention.

EXAMPLES

Some particular embodiments of the present invention are shown as an example in FIG. 1 to 4, without limiting the invention.

FIGS. 1A, 1B, 1C and 1D show side views of caps having a clip, wherein FIG. 1A is a cap (1) having a clip designed as a hexagonal ring spanner (2), FIG. 1B is a cap (3) having a clip (4) designed as a spanner comprising a ring of rubber (5), which fits form- and force-locking with the needle assembly, FIG. 1C is a cap (6) having a flexible clip (7) designed as a ring spanner, FIG. 1D is a cap (8) having a flexible clip (9) designed as a spanner comprising a partial ring of rubber (10).

Figure 2B:
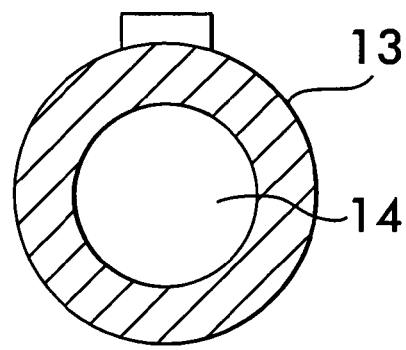

FIGS. 2A and 2B show a top view of the cap, whereby the front side of the cap comprises the receiving bore designed as and having the function of a box spanner. FIG. 2A shows a top view of the cap (11) in which the receiving bore (12) is hexagonally designed, whereas in FIG. 2B the receiving bore (14) of the cap (13) is designed like a ring spanner.

Figure 3A:
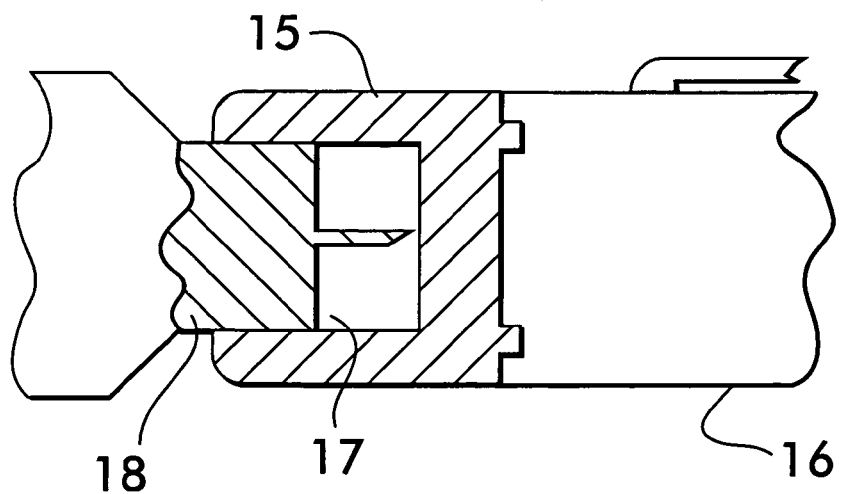
Figure 3B:
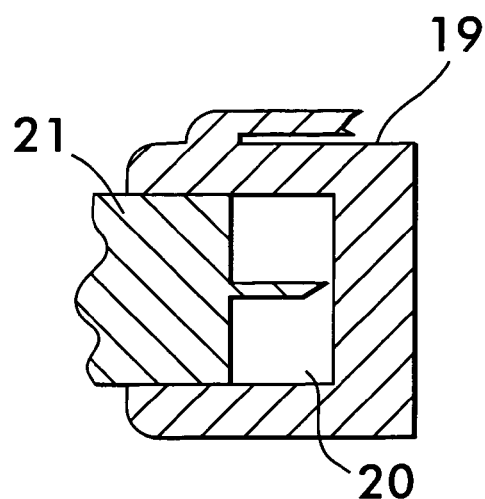

FIGS. 3A and 3B show a side view of the cap having the receiving bore on the front side. FIG. 3A shows a side view of a form- and force-locking attachment (15) of the cap (16), which serves as a receiving bore (17) of the needle assembly (18). FIG. 3B shows a side view of the cap (19), which services as a receiving bore (20) or the needle assembly (21).

FIGS. 4A, 4B, 4C, 4D and 4E show a side view of a cap (22, 23, 24) having the receiving bore on an elongation on the distal end of the cap (25, 26, 27). FIG. 4A shows such an elongation having a receiving bore (28) corresponding to FIG. 1A. FIG. 4B shows such an elongation having a receiving bore (29) corresponding to FIG. 1B. FIG. 4C shows a section view of FIG. 4A. FIG. 4D shows a section view of FIG. 4B. FIG. 4E shows such an elongation having a receiving bore (30) according to a ring spanner.

The invention claimed is:

1. A one-piece cap for an injection device, wherein said injection device comprises an exchangeable needle assembly, and wherein said cap can be fixed on the device in order to cover the said exchangeable needle assembly, and wherein the said cap comprises a receiving bore, characterized in that, the said cap having the receiving bore receives the said needle assembly, and wherein the said cap may be used as a tool for mounting and demounting the said needle assembly, and wherein the said cap has a clip with an opening in the shape of a hexagonal ring spanner for mounting and demounting the said needle assembly.

2. An injection device comprising a cap according to claim 1.

3. An exchangeable needle assembly having the geometry of a hexagonal screw or bolt, and which fits to the receiving bore of the cap according to claim 1.

4. A kit comprising a cap according to claim 1, an exchangeable needle assembly having the geometry of a hexagonal screw or bolt that fits to the receiving bore of the cap, an injection device, or a combination thereof.

* * * * *